United States Patent [19]

Wang et al.

[11] Patent Number: 4,879,211

[45] Date of Patent: * Nov. 7, 1989

[54] RAPID IMMUNOAGGLUTINATION TEST FOR PRESENCE OF HIV IN BODY FLUIDS

[75] Inventors: Chang Y. Wang, Long Island; James J. G. Wang, Flushing, both of N.Y.

[73] Assignee: United Biomedical Inc., Lake Success, N.Y.

[*] Notice: The portion of the term of this patent subsequent to Apr. 5, 2005 has been disclaimed.

[21] Appl. No.: 126,269

[22] Filed: Nov. 30, 1987

[51] Int. Cl.⁴ .......................................... G01N 33/569
[52] U.S. Cl. ............................................. 435/5; 435/7; 435/805; 435/810; 436/518; 436/531; 436/809; 436/810; 436/811
[58] Field of Search ...................... 435/5, 7, 805, 810; 436/518, 531, 809–811

[56] References Cited

U.S. PATENT DOCUMENTS

| | | | |
|---|---|---|---|
| 4,520,113 | 5/1985 | Gallo et al. | |
| 4,725,669 | 2/1988 | Essex et al. | 530/322 |
| 4,735,896 | 4/1988 | Wang et al. | 435/5 |
| 4,748,110 | 5/1988 | Paul | 435/5 |

FOREIGN PATENT DOCUMENTS 233061  8/1987  European Pat. Off. ................ 435/5

OTHER PUBLICATIONS

Riggen et al., "Detection of Anitbodies to Human Immunodeficiency Virus by Latex Agglutination with Recombinant Antigen", J. Clin. Microbiology, 25 (9) 1772-3 (Sep. 1987).
Hahn et al., Nature, 312, 155–169 (nov. 1984).
Wang et al., Proc. Nat. Acad. Sci. U.S.A., 83, 6159–6163 (Aug. 1986).
McDougal et al., J. of Immunolog. Methods, 76, 171–183 (1985).
Bulletin by E. I. duPont Nemours Inc., Biotechnology Update.
Bulletin by V-Tech Inc. (Sep. 1985).
Quash et al., J. Immunolog. Methods, 22, 165–174 (1978).
Prowse et al., Immunochem., 15, 429–436 (1978).
Bio-Rad Bulletin (1984).

Primary Examiner—Christine M. Nucker
Attorney, Agent, or Firm—Morgan & Finnegan; Maria C. H. Lin

[57] ABSTRACT

The present invention relates to a rapid immunoagglutination method for direct determination of the presence of HIV in body fluids to detect early injectio by HIV. The method employs polyclonal anti-HIV IgG purified from the sera of known HIV injected individuals and absorbed onto carboxylate modified latex beads.

3 Claims, 3 Drawing Sheets

RAPID IMMUNOAGGLUTINATION TEST FOR PRESENCE OF HIV IN BODY FLUIDS

INTRODUCTION

The present invention relates to an immunodiagnostic test for the presence of HIV in body fluids. More particularly, it is directed to a rapid immunoagglutination test using anti-HIV IgG to determine the presence of HIV itself in body fluids.

BACKGROUND

Human immunodeficiency virus (HIV), previously named human T-cell lymphotropic virus-III (HTLV-III), a human retrovirus has been found to be the causative agent of the acquired immunodeficiency syndrome (AIDS)[1].

AIDS is a devastating, death threatening disease and has spread alarmingly in Africa, the Carribean basin, Unites States, Europe and throughout the world. Based on existing knowledge, the disease is spread through sexual contact, transfusion of contaminated blood, and sharing of unsterilized needles. The mortality rate of the disease is very high, approximately 70% of those who manifest symptoms of the disease have died, no effective or preventive measures against the infection by HIV has been found. It is, therefore, imperative that the population be educated on the dangers of the disease, and the manner of transmission. Most importantly, the blood supply for those who are in need of blood transfusions, such as hemophiliacs and surgical patients, must be screened to eliminate possible contamination by HIV.

Heretofore, the presence of HIV has been determined indirectly. That is, screening tests for AIDS, AIDS Related Complex (ARC) and pre-AIDS conditions have been based on the use of the deactivated virus[2] or a synthetic peptide composition[3] described in co-pending applications Ser. Nos. 847,102 and 13,014 to detect the presence of antibodies to HIV. From the presence of antibodies to HIV, it is inferred that the sample biological body fluid would contain the antigen, HIV.

Detection of HIV itself has been principally based on the rather cumbersome reverse transcriptase assay.

In 1985, J. S. McDougal et al. reported a sandwich enzyme-linked immunoassay (ELISA) for detecting HIV[4]. The method involved the collection of IgG fraction from a serum sample with high titer antibody to HIV obtained from a homosexual with chronic unexplained lymphadenopathy. The IgG fraction was purified by ammonium sulfate precipitation and diethylaminoethyl cellulose chromatography. A portion of the IgG fraction was coupled with fluorescien isothiocyanate (FITC). Another portion was coupled to horseradish peroxidase (HRPO).

The FITC-anti-HIV at 19 ug/ml was incubated with HIV in disrupted cultured cells and found to react specifically with HIV and become stained. The entire process takes at least about two to three hours.

Alternatively, an IgG fraction was used to coat a 96-well microtiter tray. HIV cultured cell supernates were mixed with buffer and added to the wells and incubated at 4° C. overnight. HRPO-anti-HIV was added to each well and caused to react with o-phenylene-diamine (OPD) to give a colored product. The entire ELISA procedure takes approximately one day.

Another method for direct detection of HIV has been reported[5]. This method utilizes rabbit polyclonal anti-HIV fixed on microtiter plate wells to capture the HIV p24 protein. The captured protein is complexed with biotinylated rabbit polyclonal anti-HIV p24 and probed with a streptavidin-horseradish peroxidase conjugate. The complex is then detected by incubation with orthophenyl-diamine to produce a yellow color in positive wells.

The method calls for immunization of rabbits with HIV, harvesting and purifying the rabbit anti-HIV polyclonal antibodies which is very time consuming.

Agglutination tests using latex beads are known. For example, agglutination has been used in diagnostic tests to determine pregnancy[6] and measles[7].

However, up to the present, agglutination has not been found to be applicable as a means for the diagnosis of HIV infection in body fluids.

Up to the present, no rapid simple assays have been developed for the direct detection of HIV.

It is the object of the present invention to develop a rapid and simple screening test for the direct determination of HIV in body fluids.

REFERENCES

1. Beatrice Hahn et al., Nature, 312, pp. 166. (Nov. 1984)
2. R. C. Gallo et al. U.S. Pat. No. 4,520,113.
3. J. J. G. Wang et al. Proc. Natl Acad. Sci. USA, 83, pp. 6159–6163 (Aug. 1986).
4. J. S. McDougal et al., J. of Immuno. Methods, 76, pp. 171–183 (1985).
5. Bulletin by E. I. duPont de Nemours Inc., in Biotechnology Update, [date] p. 16.
6. Bulletin by V-Tech, Inc. September 1985.
7. G. Quash et al., J. Immun Methods, 22, pp. 165–174 (1978).

BRIEF DESCRIPTION OF THE INVENTION

According to present invention, a rapid immunoagglutination method for the direct determination of the presence of HIV in body fluids comprising:

A. Preparing, by affinity chromatography over a protein A column, purified polyclonal anti-HIV IgG from serum, which had been previously determined to be positive for antibodies to HIV and negative for antibodies to HBsAg, HTLV-I, HBcAg and EBV, B. Adsorbing the purified polyclonal anti-HIV IgG on to carboxylate modified latex beads having a particle size of about 1 um in diameter;

C. Mixing on a slide, a drop of unknown serum with a drop of 0.01M PBS buffer at a pH of about 7.0;

D. Mixing on a second slide, a drop of normal serum with the same buffer;

E. Adding to each slide a drop of 0.01M PBS buffer containing from about 0.2% (weight:volume) of the latex beads adsorbed with purified polyclonal anti-HIV IgG;

F. Allowing the slides to incubate at room temperature for about 0.5 to about 2.5 minutes;

G. Examining the slides within about three minutes from step (E) visually to determine the degree of agglutination of the unknown serum sample compared to the normal serum.

The examination may be made by the naked eye or under a microscope.

DETAILED DESCRIPTION OF THE INVENTION

Figure 1:
FIG. 1 is a photograph of a suspension of 0.2% (wt:vol) latex beads coated with polyclonal anti-HIV human IgG in 0.01M PBS at pH 7.2 under 100× magnification.

In accordance with the present invention, a rapid immunoagglutination method for the direct determination of HIV in body fluids comprises:

A. Preparing, by affinity chromotography over a protein A column, purified polyclonal anti-HIV IgG from serum which had been previously determined to be positive for antibodies to HIV and negative to antibodies to HBsAg, HTLV-I, HBcAg and EBV;

B. Adsorbing the purified polyclonal anti-HIV IgG on to carboxylate modified latex beads having a particle size of about 1 um in diameter;

C. Mixing on a slide, a drop of unknown serum with a drop of 0.01M PBS buffer at a pH of about 7.0;

D. Mixing on a second slide, a drop of normal serum with the same buffer;

E. Adding to each slide a drop of 0.01M PBS buffer containing from about 0.2% (weight:volume) of the latex beads adsorbed with purified polyclonal anti-HIV IgG;

F. Allowing slides to incubate at room temperature for about 0.5 to about 2.5 minutes;

G. Examining the slides with about three minutes from step (E) visually to determine the degree of agglutination of the unknown serum sample compared to the normal serum.

The purification of IgGs from serum containing polyclonal antibodies, or from ascites fluid containing a mixture of monoclonal antibodies directed toward HIV can also be achieved by salt precipitation followed by ionic exchange chromatography. The processes uses common methods practiced by immunochemists for IgG purification.

According to the present invention, polyclonal anti-HIV IgG was obtained from HIV infected individuals whose sera which have been shown to have high titers of antibodies to HIV.

Substantially pure polyclonal anti-HIV human lgG can be prepared as follows.

Serum samples which have been determined to be positive for antibodies to HIV are collected. The serum samples were tested and shown to be positive for anti-HIV by enzyme immunoassay (EIA) using as the immunoadsorbent deactivated virus as shown in Gallo, U.S. Pat. No. 4,520,113, or a synthetic peptide with 21 amino acids or a mixture of synthetic peptides as described in applicant's prior application Ser. Nos. 847,102 and 13,014, or as being anti-HIV positive by the Western Blot Method (WB). The descriptions of the synthetic peptide and their use as immunoadsorbents for EIA testing can be found in application Ser. Nos. 847,102 and 13,014, the contents of which are hereby fully incorporated herein.

These serum samples were also determined to be negative for antibodies to HTLV-I hepatitis B surface antigen (HBsAg), hepatitis B core antigen (HBcAg), and Epstein-Barr virus (EBV) by ELISA using the respective antigens as solid phase immunoadsorbents. The serum samples should be negative for antibodies to HTLV-I, HBsAg, HBcAg, and EBV to remove any IgG which may be cross reactive with HIV.

Since the serum samples show only antibodies specific to HIV, the polyclonal anti-HIV human IgG obtained from the serum samples should be highly pure and react specifically with HIV or epitopes therefor. This is, indeed, shown to be true as demonstrated in FIG. 6 and Example 5, Table II.

The serum samples were then pooled and heated at 56° C. for about 60 minutes. NP40, a detergent known to deactivate HIV was added so that the final concentration of NP40 in the pooled sera was bout 0.5% (v:v). The treated pooled sera sample was filtered through a 0.22 u Millipore ® filter and then tested by EIA using either an HIV viral lysate or a mixture of synthetic peptides having a 21mer peptide, a 19mer peptide and an 11mer peptide as the immunoadsorbent as described in Ser. No. 013,014.

The pooled sera sample can be purified by using an affinity protein A column which specifically binds human IgG. For the present development, an Affi-Gel ® Protein A MAPS Kit (Bio-Rad, Richmond, Calif.) was used to prepare the column. Other purification methods such as salt precipitation followed by ion exchange chromatography may also be used.

Using the process of the present invention described above, substantially pure polyclonal anti-HIV IgG can be obtained from a readily available source, serum from HIV infected patients. The purification process is fast and can yield a large quantity of substantially pure polyclonal anti-HIV IgG.

1 mg of purified polyclonal anti-HIV IgG being sufficient to be adsorbed onto 10 mg of carboxylated, modified polystyrene latex beads to produce 100 ml of a 1% (w:v) suspension in 0.01M PBS containing 0.5% as bovine serum albumin and 0.1% sodium azide as a stock reagent. For immunoagglutination assays, the stock solution is diluted 1:5 with the same buffer to a 0.2% (w/v) suspension.

The immunoagglutintion assay is simple and rapid to perform. The results can be obtained within about 0.5 to 3 minutes.

Three clean glass microscope slides were used. A drop of a buffer solution, 0.01M PBS pH 7.2, was placed on each slide. A drop of buffer solution, a normal serum sample as control, and a sample of AIDS patient serum was introduced on each slide respectively. The slides were swirled gently to mix the buffer with the samples. A drop of the 0.2% (w/v) anti-HIV IgG adsorbed latex beads suspension in a mixture of 0.01M PBS, 0.5% BSA and 0.1% sodium azide, pH 7.2 was added to each of the three slides. The slides were again gently swirled to mix the samples with the suspension. The slides are then allowed to stand at room temperature for about 0.5 to about 3 minutes. Before the slides become dry, within about 3 minutes, the slides are observed under a microscope (Olympus Model) at about 100× magnification.

It is observed that in the AIDS patient serum sample containing HIV the beads agglutinate to form larger particles, whereas, on the slide with buffer only and a normal serum sample, a uniform suspension of latex beads is observed.

The procedure according to the present invention is highly specific and sensitive. The agglutination test shows that the latex beads adsorbed with polyclonal anti-HIV IgG react only with HIV and HIV peptides and does not react with unrelated peptides derived from other sources such as $DW_{10}$ peptide, a peptide representing a portion of the amino acid sequence of the human HLA-DR molecule, and a BCGF peptide with its sequence derived from the C-terminal of the murine B cell growth factor molecule. THe test is highly sensitive, the optimum concentration of HIV tested is about 38 pg virus per 10 ul. (See Example 3).

The agglutination test according to the present invention being highly specific and sensitive has been shown to be effective in detecting the HIV in HIV infected individuals in the asymptomatic stage prior to anti-HIV detection (See Example 7). Thus, it provides a tool for early detection of HIV infection, which was heretofore unavailable. The agglutination test according to the present invention eliminates the problem of non-detectability of early infection. However because the body can produce sufficient antibodies to HIV to react with all of the HIV in the body, the agglutination test should be employed in conjunction with an EIA test for detecting antibodies to HIV to confirm infection by HIV.

The following examples illustrate the present invention but are not to be construed as limiting the scope of the invention.

EXAMPLE 1

Preparation of Polyclonal Anti-HIV Human IgG

Fourteen serum samples with high titer of antibodies to HIV and negative for antibodies to HTLV-I, HBsAg, HBcAg and EBV were collected.

The pooled serum sample, a total of 560 ml, was heated at 56° C. for about 60 minutes and 2.8 ml of NP40 was added for a final concentration of 0.5% (v:v) NP40. The treated sera sample was then filtered through a 0.22 u Millipore ® filter.

An affinity protein A column was prepared using an Affi-Gel ® Protein A MAPS kit (Bio-Rad, Richmond, Calif.). A 10 cm × 1 cm column was packed with Agarose beads and coated with 5 ml of the Affi-Gel ® Protein A provided in the kit. The column was equilibrated with 25 ml of the binding buffer provided in the kit.

5 ml of the treated and filtered sera sample was mixed with 5 ml of the binding buffer. The diluted sera sample was filtered through a 0.22 u Millipore ® filter and then applied to the column. The effluent was allowed to flow at a rate of about 1 ml/min. The column was washed with 75 ml of the binding buffer until the absorbance at 280 nm was below at 0.05 O.D. units. The column was then eluted with 75 ml of a 0.1M citrate buffer, pH 3.0. The eluent was collected into individual tubes of a fraction collector connected to a photometric monitor set at 280 nm. Each tube of the fraction collector contained 0.5 ml of 1M TRIS buffer pH 9.0 to neutralize the citrate buffer.

The fraction was tested by Western Blot analysis with HIV lysate. The purified anti-HIV human IgG contained antibodies to all of the protein components associated with HIV, e.g. gp41, gp120, gp160, p24, p55, p17, etc.

EXAMPLE 2

Adsorption of Purified Polyclonal Anti-HIV Human IgG On Latex Beads 10 mg of carboxylate modified latex beads, white, having a uniform average particle size of 1.072±0.003 um and 5% by weight of solids in 0.01M PBS, pH 7.0 (Serogen Diagnostics, Indianapolis, Ind.) was washed with distilled water three or four times. The wash was removed by centrifuge. The beads were then suspended in 1 ml 0.1M carbonate buffer, pH 9.5.

1 mg of polyclonal anti-HIV human IgG purified was dissolved in 1 ml of 0.1M carbonate buffer, pH 9.5. This was mixed with the latex beads suspension and placed in a constant temperature water bath at 40° C. for about 1.50 hours.

The beads suspension was centrifuged, the supernatant removed and washed three times with 0.01M PBS buffer pH 7.2, containing 0.05% (v:v), Tween. The wash solution was removed each time by centrifuge.

EXAMPLE 3

Agglutination Assay With Polyclonal Anti-HIV Human IgG Adsorbed on Latex Beads

Figure 2:
FIG. 2 is a photograph of a suspension similar to FIG. 1 with pooled normal serum under the same magnification as FIG. 1.
Figure 3:
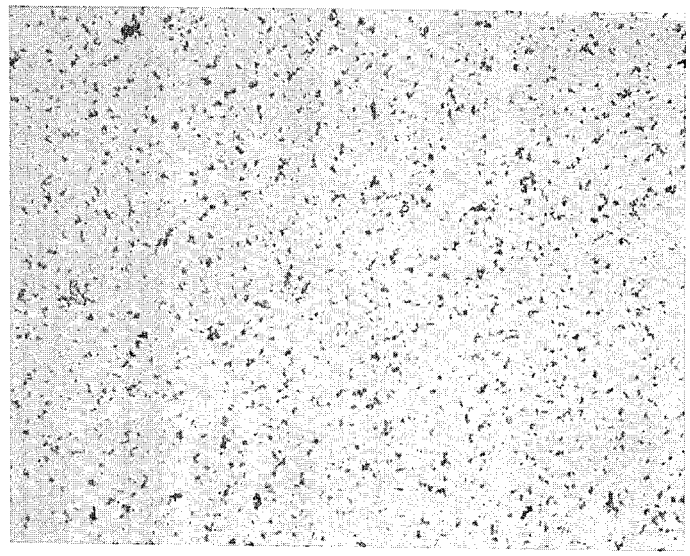
FIG. 3 is a photograph of a suspension similar to FIG. 1 with AIDS positive serum sample under the same magnification as FIG. 1.
Figure 4:
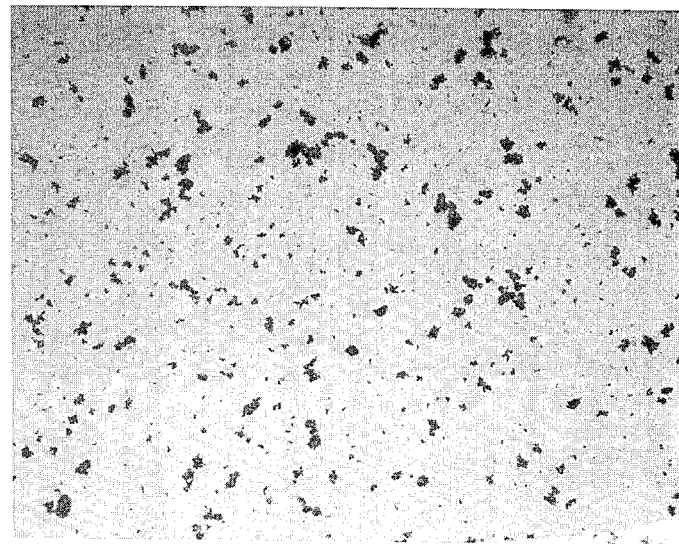
FIG. 4 is a photograph of a suspension similar to FIG. 1 with a second AIDS positive serum sample under the same magnification as FIG. 1.
Figure 5:
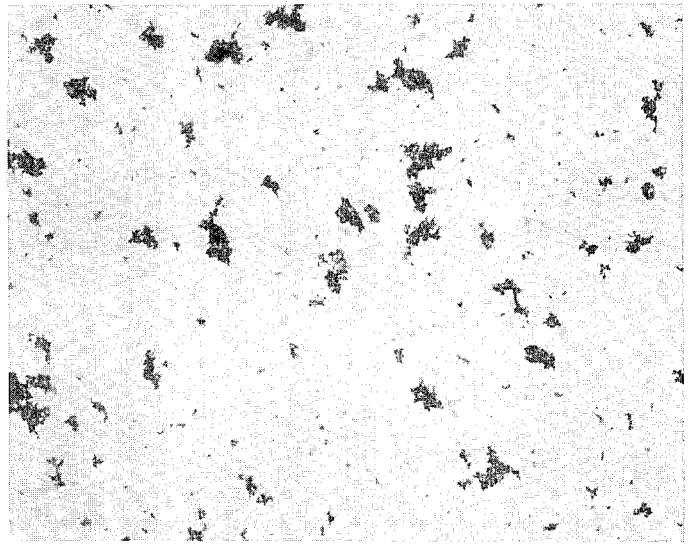
FIG. 5 is a photograph of a suspension similar to FIG. 1 with a third AIDS positive serum under the same magnification.

The 1% stock suspension of the latex beads adsorbed with anti-HIV IgG was diluted 1:5 to 0.2% (w:v) with 0.01M PBS buffer, pH 7.2. On each of three microscope glass slides was placed one drop of 0.01M PBS buffer, pH 7.2. On each of the three slides was placed respectively one drop each of the same buffer, normal serum and test serum sample. The slides were gently swirled to mix the drops. Then one drop of the 0.2% (w:v) suspension of latex beads pre-coated with Anti-HIV IgG was added to each of the three slides. Each of the slides were gently swirled to mix the suspension with the solution. The slides were allowed to stand for about 1 minute and then examined at 100× magnification under a microscope. The degree of agglutination was determined visually as shown in FIGS. 1-5.

The optimal detection limit was found to be about 38 pg of HIV in a 10 ul sample.

EXAMPLE 4

A panel of thirty-two serum samples from AIDS patients were analyzed by the agglutination procedure described in Example 3. The results were compared with EIA results using as immunoadsorbents either the deacted HIV viral lysate or a mixture of three synthetic peptides, a 21 mer peptide, a 19 mer peptide, both from the p41 region and a 11 mer peptide from the p24 region 10:1:1 as the coating antigens. The results are shown in Table 1.

TABLE I

| Sample | Agglutination* Test | $A_{492}$ Deactivated Virus | $A_{492}$ Peptides Mixture |
| --- | --- | --- | --- |
| 1 | + | over 2 | over 2 |
| 2 | + | 1.894 | over 2 |
| 3 | +++ | over 2 | over 2 |
| 4 | + | 1.893 | over 2 |
| 5 | +++ | over 2 | over 2 |
| 6 | ++ | over 2 | over 2 |
| 7 | +++ | over 2 | over 2 |
| 8 | ++ | 1.785 | over 2 |
| 9 | + | over 2 | over 2 |
| 10 | + | 1.940 | over 2 |

TABLE I-continued

| Sample | Agglutination* Test | $A_{492}$ Deactivated Virus | $A_{492}$ Peptides Mixture |
|---|---|---|---|
| 11 | + + | over 2 | over 2 |
| 12 | + + | 1.490 | over 2 |
| 13 | ± − + | over 2 | over 2 |
| 14 | + + | 1.628 | over 2 |
| 16 | + − + + | over 2 | over 2 |
| 17 | + | over 2 | over 2 |
| 18 | + | 1.572 | over 2 |
| 19 | + | over 2 | over 2 |
| 20 | + − + + | over 2 | over 2 |
| 21 | + + + | 1.931 | over 2 |
| 22 | + | 1.452 | over 2 |
| 23 | + + | over 2 | over 2 |
| 24 | ± | over 2 | over 2 |
| 25 | + | 1.616 | over 2 |
| 26 | + | 1.687 | over 2 |
| 27 | + + | over 2 | over 2 |
| 28 | ± − + | over 2 | over 2 |
| 29 | + + | over 2 | over 2 |
| 30 | ± − + | 1.492 | over 2 |
| 31 | + + | 1.642 | over 2 |
| 32 | + + + | 1.683 | over 2 |

*"+" indicates degree of agglutination.
"±" indicates a weak degree agglutination.

EXAMPLE 5

Specificity and Sensitivity of the Agglutination Test

The agglutination test was used against a 21 mer peptide, a 35 mer peptide, (both shown to be specific for antibodies to HIV), a $DW_{10}$ peptide (a 17 mer peptide with its sequence derived from a section of the amino acid sequence of the human HLA Dw10 beta chain molecule), a BCGF peptide (a 20 mer peptide with its amino acid sequence derived from the predicted amino acid sequence of the murine B cell growth factor), and deactiviated HIV. The results are shown in Table II.

TABLE II

| Test Reagent | Dilution | Amount in 10 ul | Reactivit |
|---|---|---|---|
| 21 mer peptide | 1/8 | 12.5 ng | + |
| 35 mer peptide | 1/16 | 6.25 ng | + |
| $DW_{10}$, 17 mer peptide | undiluted | 100 ng | − |
| BCGF, 20 mer peptide | undiluted | 100 ng | − |
| HIV | 1/1,310,720 | 38 pg | + |

These results show that the agglutination test is specific to HIV or antigenic peptides derived from HIV.

EXAMPLE 6

Agglutination Test of Sera from Homosexuals

Nine serum samples were obtained from Long Island Jewish Hospital. Thse nine samples were identified as being from "healthy" homosexuals.

TABLE III

| Sample | EIA $A_{492}$ | Agglutination Test |
|---|---|---|
| 1 | − | − |
| 2 | 2.00 | − |
| 3 | − | + + + |
| 4 | 2.00 | + + |
| 5 | 2.00 | + + + |
| 6 | 2.00 | + |
| 7 | − | − |
| 8 | − | − |
| 9 | − | − |

The above results show that the agglutination test correlates only partially with the HIV antibody test in this group of high risk individuals. Among the nine samples tested, only seven of them (1, 4, 5, 6, 7, 8, 9) are in agreement. This is due to the known dynamics of the response to HIV infection. Antibodies to HIV only develop after a period of time upon infection by HIV antigen. However, following the development of antibodies, formation of antigen-antibody complexes can lead to antigenemia. The presence of HIV antigen in serum sample #3 as detected by the agglutination test indicates probable early HIV infection. This is further shown by the results obtained in Example 7, Table IV.

EXAMPLE 7

A series of nine serum specimens were collected over a period of five months on various dates from a HIV infected patient who seroconverted. The specimens were tested for presence of HIV antibodies by EIA using the synthetic peptide mixture described in co-pending application Ser. No. 013,014, and by the agglutination assay of the present invention.

The results are shown in Table IV.

TABLE IV

| Sample ID | Date Collected | $A_{492}$ EIA Peptides Test | Agglutination Test |
|---|---|---|---|
| BB1 1 | 5/4/84 | 0.04(−) | + + |
| BB1-2 | 7/8/84 | 0.04(−) | + |
| BB1-3 | 7/29/84 | 0.08(−) | + |
| BB1-4 | 8/19/84 | 0.26(+) | + |
| BB1-5 | 9/2/84 | 0.65(+) | − |
| BB1-6 | 9/9/84 | 0.85(+) | − |
| BB1-7 | 9/16/84 | 0.86(+) | − |
| BB1-8 | 9/23/84 | 1.05(+) | − |
| BB1-9 | 10/14/84 | 1.51(+) | − |

The first four specimens gave clear positive detection of HIV antigen by the agglutination test whereas the last five specimens gave negative detection for HIV. On the contrary, by EIA the first three specimens were negative, and the last six specimens were clearly positive. This confirms that that agglutination test provides a method for detection of early infecton by HIV. Furthermore, the combination of the agglutination test of the present invention with an EIA HIV antibodies test will aid in the accurate detection and diagnosis of infection by HIV.

We claim:
1. An immunoagglutination method for the detection of the presence of HIV body fluids comprising:
   A. Preparing substantially pure polyclonal anti-HIV IgG from serum which had been previously determined to be positive for antibodies to HIV and negative to antibodies to HTLV-I, HBsAg, HBcAg and EBV by (i) affinity chromatography over a protein A column; wherein protein A is coupled to crosslinked agarose beads via chemically stable amide bonds; or (ii) salt precipitation followed by ion exchange chromatography;
   B. Adsorbing the substantially purified polyclonal anti-HIV IgG on to carboxylate modified latex beads having a particle size of about 1 um in diameter;
   C. Mixing on a slide, a drop of unknown serum with a drop of 0.01M PBS buffer at a pH of about 7.0;
   D. Mixing on a second slide, a drop of normal serum with the same buffer;

E. Adding to each slide a drop of 0.01M PBS buffer containing from about 0.12% weight:volume of the latex beads absorbed with purified polyclonal anti-HIV IgG;

F. Allowing the slides to incubate at room temperature for about 0.5 minutes to about 2.5 minutes;

G. Examining the slides within about three minutes from step (E) to determine the degree of agglutination, of the unknown serum sample compared to the normal serum wherein the presence of virus is shown by the agglutination of the latex beads to from larger particles.

2. An immunoagglutination method according to claim 1 wherein the polyclonal anti-HIV IgG was purified by using affinity chromatography over a protein A column.

3. An immunoagglutination method according to claim 1 wherein the polyclonal anti-HIV IgG was purified by salt precipitation followed by ion exchange chromatography.

* * * * *